(12) United States Patent
Brieva et al.

(10) Patent No.: US 6,214,329 B1
(45) Date of Patent: Apr. 10, 2001

(54) MASCARA COMPOSITIONS AND METHOD FOR CURLING LASHES

(75) Inventors: Hernando Brieva, Manalapan; Kristine Patel, Kenilworth; Julio Gans Russ, Westfield; Ida Marie Sandewicz, Monroe Township; Tian Xiang Wang, Edison, all of NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/326,458

(22) Filed: Jun. 7, 1999

(51) Int. Cl.$^7$ .................. A61K 7/06; A61K 6/00
(52) U.S. Cl. .............. 424/70.7; 424/70.7; 424/70.11; 424/70.17; 424/401; 424/63
(58) Field of Search ............... 424/70.7, 401, 424/70.1, 70.9, 70.11, 70.17, 63

(56) References Cited

U.S. PATENT DOCUMENTS

| | | | |
|---|---|---|---|
| 3,969,087 | * 7/1976 | Saito et al. | 44/7 |
| 4,423,031 | 12/1983 | Murui | 424/63 |
| 5,154,916 | 10/1992 | Arraudeau | 424/63 |
| 5,474,778 | 12/1995 | Ichikawa | 424/401 |
| 5,843,407 | 12/1998 | El-Nokaly | 424/64 |
| 5,874,072 | 2/1999 | Alwattari | 424/70.7 |
| 5,876,704 | * 3/1999 | Collin et al. | 424/70.7 |

FOREIGN PATENT DOCUMENTS 898 953    3/1999   (EP) .

OTHER PUBLICATIONS

Ajinomoto Co., Inc., Amino Acid Gelatinization Agent, Jan. 1998.
Aqualon Product Data, Natrosol Plus CS., Grade 330, Oct. 1992.

* cited by examiner

Primary Examiner—Thurman K. Page
Assistant Examiner—Susan Tran
(74) Attorney, Agent, or Firm—Julie Blackburn

(57) ABSTRACT

A pigmented emulsion composition for application to eyelashes or eyebrows comprising an aqueous phase and a non-aqueous phase, wherein the non-aqueous phase comprises at least one organic, solid, non-polymeric gelling agent, which is capable of gelling the pigmented emulsion composition to a viscosity of 4,000 to 2,000,000 centipoise at 25° C., and a method for lengthening, coloring, and curling eyelashes using said composition.

18 Claims, No Drawings

MASCARA COMPOSITIONS AND METHOD FOR CURLING LASHES

TECHNICAL FIELD

The invention is in the field of compositions for application to the eyelashes and eyebrows.

BACKGROUND OF THE INVENTION

Mascara is a very popular cosmetic with women who wish to color, thicken, and accentuate the eyelashes. A "gold standard" mascara should provide optimal length, color, thickness, and curl to the lashes. Cosmetic manufacturers are consistently working to improve mascara formulas so that these attributes are maximized.

One key ingredient in mascara formulas, namely wax, is believed to play a role in achieving all of the attributes mentioned above. That is why virtually all mascaras contain wax. However, waxes provide certain undesireable properties. In particular, waxes cause mascaras to increase in viscosity with storage. When mascaras are first made, the waxes in the formula are only partially solvated, or reacted, with the solvent which is present. As time passes, the solvent present in the formula continues to react with the wax so that eventually the amount of free solvent is nearly all reacted. The reduction of free solvent in the formula causes an increase in viscosity of the formula, sometimes to a level which makes it difficult to use and apply. This causes problems for manufacturers because such mascaras have a reduced shelf life. Thus, it is desired to formulate mascaras that contain reduced levels of wax, or no wax at all, so that the above storage problems are eliminated. At the same time those mascaras must color, lengthen, thicken, and curl the eyelashes as well or better than the currently available formulas.

U.S. Pat. No. 5,389,363 teaches mascara compositions which lengthen, color and curl eyelashes. The composition taught therein is an oil in water emulsion containing a gel phase. The formula is believed to contribute to curling as well as coloring and accentuating the eyelashes. The composition also contains waxes, which are necessary to thicken lashes, enhance film formation, and cause lash curling.

The object of the invention is to provide a mascara composition that provides long lasting color and at the same time curls the lashes.

Another object of the invention is to provide a gel based mascara, i.e. a mascara where the viscosity traditionally achieved with waxes is instead achieved in whole or in part with non-wax gelling agents.

Another object of the invention is to provide a method for lengthening, coloring, and curling eyelashes.

Another object of the invention is to provide a mascara composition that contains minimal amounts of animal, vegetable, or mineral waxes, or where such waxes are not present at all.

Another object of the invention is to provide a mascara formula that exhibits reduced thickening with time, but still provides acceptable application, wear, and aesthetic properties.

SUMMARY OF THE INVENTION

The invention is directed to a pigmented emulsion composition for application to eyelashes or eyebrows comprising an aqueous phase and a non-aqueous phase, wherein the non-aqueous phase comprises at least one organic, solid, non-polymeric gelling agent, which is capable of gelling the pigmented emulsion composition to a viscosity of 4,000 to 2,000,000 centipoise at 25° C.

The invention also comprises a method for lengthening, coloring and curling eyelashes comprising applying to said eyelashes a pigmented emulsion composition for application to eyelashes or eyebrows comprising an aqueous phase and a non-aqueous phase, wherein the non-aqueous phase comprises at least one organic, solid, non-polymeric gelling agent, which is capable of gelling the pigmented emulsion composition to a viscosity of 4,000 to 2,000,000 centipoise at 25° C.

DETAILED DESCRIPTION

All percentages mentioned herein are percentages by weight unless otherwise indicated. The pigmented emulsion composition of the invention is for application to eyelashes and eyebrows to cause coloring, conditioning, and in the case of eyelashes, curling. Preferably, the pigmented emulsion composition is gel-based, which means that the viscosity of the mascara is controlled by non-wax gelling agents rather than the animal, vegetable, or mineral waxes which are traditionally used in such formulas for that purpose. The composition of the invention comprises an aqueous phase and a non-aqueous phase.

I. The Non-Aqueous Phase

The emulsion compositions of the invention comprise 0.1–99%, preferably 0.5–90%, more preferably 1–80% by weight of the total composition of a non-aqueous phase. The term "non-aqueous phase" means a phase comprised of one or more ingredients which are water insoluble, and thus are not soluble in the aqueous phase of the composition. Generally, such non-aqueous phase ingredients will include lipophilic, non-polar or slightly polar materials such as waxes, hydrocarbons, fats, oils, and the like, in addition to one or more organic, solid, non-polymeric gelling agents. Generally, the non-aqueous phase may be the continuous or dispersed phase in the emulsion composition such that the composition is a water-in-oil or oil-in-water emulsion. Preferably, the composition of the invention is an oil-in-water emulsion where the non-aqueous phase forms the dispersed phase in the emulsion composition. The non-aqueous phase comprises at least one organic, solid, non-polymeric gelling agent which is capable of gelling the entire composition to a viscosity of 4,000 to 2,000,000; preferably 40,000 to 1,500,000; more preferably 100,000 to 1,000,000 centipoise at 250 C. The organic, solid, non-polymeric gelling agent may be the sole ingredient in the non-aqueous phase, or this phase may comprise other ingredients, preferably lipophilic, non-polar ingredients such as oils, fats, waxes, and similar materials. Generally, if the non-aqueous phase comprises the gellant in combination with other non-polar ingredients, the mixture of ingredients will form a single homogeneous phase or dispersion when heated to a temperature ranging from about 28 to 250° C. and cooled to room temperature (25° C.). These ingredients are further described below.

A. Organic, Solid, Non-Polymeric Gelling Agent

The composition of the invention comprises 0.1–50%, preferably 0.5–30%, more preferably 1–20% by weight of the total composition, of an organic, solid, non-polymeric gelling agent or gellant. The term "solid" means that the gellant is a solid or particulate solid at 25° C. A number of gellants may be suitable for use in the compositions, including but not limited to fatty acid gellants, esters and amides of fatty acid gellants, hydroxy acids, hydroxy fatty acids, and other types of amide gellants. Examples include those set forth herein:

1. N-Acyl Amino Acids and Derivatives

Preferred gellants for use in the compositions of the invention are N-acyl amino acids and derivatives thereof, such as amides, esters, and the like. Examples of such N-acyl amino acids and derivatives are disclosed in U.S. Pat. No. 3,969,087, which is hereby incorporated by reference. These N-acyl amino acid acids and derivatives are of the following general formula:

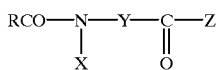

wherein RCO is an aliphatic acyl radical having 2 to 30 carbon atoms, or an aralkyl acyl radical, z is hydroxy, $NH_2$, $—OR_1$, $—NHR_2$,

and $—O—R_5NH_3^+$, where $R_1$, $R_2$, $R_3$, $R_4$ and $R_5$ are each independently a $C_{1-30}$ aliphatic hydrocarbon radical or aralkyl radical, X is hydrogen or methyl and Y is:

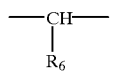

wherein $R_6$ is a $C_{1-4}$ aliphatic hydrocarbon radical, benzyl, phenyl, $—CH_2OH$,

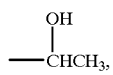

$—CH_2SH$, $—CH_2CH_2S—CH_3$, or $—(CH_2)_p—COZ$, and p is a positive integer of 1 or 2, and Z is the same as above, $—(CH_2)_mNHCOR$, where m is a positive integer of 3 to 4 and COR is the same as above or $—(CH_2)_n—$ wherein n is a positive integer of 1 to 6, with the proviso that when Z is $—OR_1$,

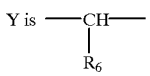

and $R_6$ is $—(CH_2)_m NHCOR$ and that at least one of $R_1$ through $R_5$ is a $C_{5-30}$ aliphatic hydrocarbon radical.

Preferably in the above composition, RCO is a $C_{12-30}$ aliphatic acyl radical, X is hydrogen, and Y is:

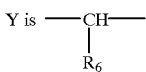

wherein $R_6$ is $—(CH_2)_p—COZ$ wherein Z is $—NHR2$.

Particularly preferred gelling agents are N-acyl amino acid amides having the following general formula:

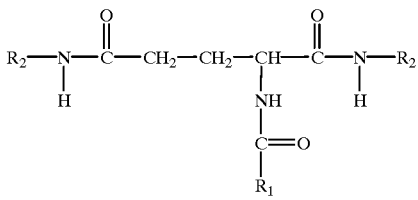

wherein $R_1$ is an aliphatic hydrocarbon radical having about 12 to 22 carbon atoms, and $R_2$ is an aliphatic hydrocarbon radical having 2 to 22 carbon atoms. The amino acids may be in the D or L form, although L-isomer are preferred. Examples of compounds embodied within the above general structure include n-lauroyl L-glutamic acid dibutyl amide, n-stearoyl-L-glutamic acid diheptyl amide, n-lauroyl-L-glutamic acid diethyl amide, n-lauroyl-L-glutamic acid dioctyl amide, N-lauroyl-L-glutamic acid didecyl amide, n-lauroyl-L-glutamic acid ditetradecyl amide, and so on. Preferred is an N-acyl glutamic acid diamide sold by Ajinomoto, referred to as N-acyl glutaric acid diamide, referred to as "GP-1". It is a white to faint yellow powder having a melting point of 155 to 163° C.

Also suitable as gelling agents are N-acyl amino acids having the above mentioned general formula. Examples of such esters include N-lauroyl-a-alanine, N-lauroyl valine, N-lauroyl gluatmic acid, $N^\alpha$, $N^\delta$-dicaproyl-ornithine and so on.

Examples of N-acyl amino acid esters include $N^\alpha$, $N^\delta$-dicaprylolylornithine octyl, decyl, lauryl and stearyl esters, $N^\alpha$, $N^\delta$dicaprylollysine octyl, decyl, and lauryl esters, $N^\alpha$, $N^\delta$ dicaprylolylysine octyl, decyl, and lauryl esters, and so on.

2. 1 2-Hydroxystearic Acid Esters and Amides Thereof

The gellant may be 12-hydroxy stearic acid, or esters or amides thereof. Such gellants comprise the following general formula:

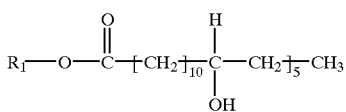

wherein $R_1$ is $OR_2$ or $NR_2R_3$; and $R_2$ and $R_3$ are each independently hydrogen or an alkyl, aryl, or arylalkyl radical which is straight or branched or cyclic and has from about 1 to 22 carbon atoms. Preferably, at least one of $R_2$ or $R_3$ is a hydrogen atom.

Examples of such gellants include 12-hydroxystearic acid, 12-hydroxystearic acid methyl ester, 12- hydroxystearic acid ethyl ester, 12-hydroxystearic acid stearyl ester, 12-hydroxystearic acid benzyl ester, 12-hydroxystearic acid amide, 12-hydroxystearic acid isopropyl amide, 12- hydroxystearic acid butyl amide, 12-hydroxystearic acid benzyl amide, 12-hydroxystearic acid phenyl amide, 12-hydroxystearic acid butyl amide, and so on.

3. Fatty Acid Esters of Di- or Trifunctional Alcohol Dimers

Preferred gellants for use in the composition are fatty acid esters of di- or trifunctional alcohol dimers. Suitable alcohols include trimethylolpropane, dimethylolpropane and the like. The dimers are prepared by reacting the trifunctional alcohol so that it forms a dimer, after which the dimer is esterified with one or more fatty acids. Preferred is a compound obtained by the esterificiation of a ditrimethylolpropane with a $C_{12-22}$ fatty acid, preferably stearic acid. This compound is is described by the proposed CTFA name ditrimethylolpropane tetrastearate and is sold by Heterene Chemical Company, Patterson, New Jersey, under the tradename HEST 2T-4S.

4. Alkylamides of Di- and Tricarboxylic Acids

Also suitable for use as gellants are alkylarnides of di- and tricarboxylic acids as set forth in U.S. Pat. No. 5,840,287, which is hereby incorporated by reference.

B. Other Non-Aqueous Phase Ingredients

The non-aqueous phase may comprise on or more non-polar liquid or solid ingredients that are soluble or dispersible in the gellant. Examples of such ingredients are set forth herein:

1. Waxes

The compositions of the invention may comprise one or more waxes. Suggested ranges include 0.1–50%, preferably 0.5–40%, more preferably 1–35% by weight of the total composition. The waxes have a melting point of about 39 to 135° C., preferably in the range of 45 to 95° C., most preferably 55 to 95° C. Suitable waxes generally includes animal waxes, plant waxes, mineral waxes, silicone waxes, synthetic waxes, and petroleum waxes. Examples of waxes in accordance with the invention include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, cetyl alcohol, beeswax, PEG-20 sorbitan beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, polyethylene, stearoxy dimethicone, dimethicone behenate, stearyl dimethicone, and the like, as well synthetic homo- and copolymer waxes such as polyethylene, PVP/eicosene copolymer, PVP/hexadecene copolymer, and the like.

In the preferred embodiment of the invention, the composition comprises less than about 10%, preferably less than 5% by weight of the total composition of waxes which are classified as animal, vegetable, or mineral waxes.

Particularly preferred is where the wax which is present in the composition is a synthetic wax which is an ethylene homopolymer or ethylene copolymer. The molecular weight of the ethylene homopolymer and/or copolymers used as the wax component may vary, so long as the melting point of the homo- or copolymer either alone or in combination is not greater than 135° C. Generally polyethylene waxes having a melting point range of 30 to 135° C. will have a molecular weight ranging from about 100 to about 2,000. Preferably the ethylene copolymers are comprised of ethylene monomer units in either repetitive or random sequence, in combination with monomer units derived from an ethylenically unsaturated comonomer of the following formula:

$$CH_2=CH-R_1$$

wherein $R_1$ is a $C_{1-30}$ straight or branched chain saturated or unsaturated alkyl, aryl, or aralkyl, preferably a $C_{1-100}$ straight or branched chain alkyl. Examples of ethylene homo- and copolymers which may be used in the invention are set forth in U.S. Pat. No. 5,556,613, which is hereby incorporated by reference.

Preferably, the composition of the invention comprise a synthetic wax either alone or in combination with a vegetable wax which is present from about 0.1 to 5%, preferably 0.5 to 2% by weight of the total composition. The preferred synthetic wax is polyethylene having a molecular weight of about 400 and a melting point of 79.5° C., which is sold by New Phase Technologies under the tradename Performalene 400 Polyethylene. Particularly preferred is wherein the vegetable wax is rice wax.

2. Oils

If desired, the composition of the invention may comprise one or more oils. Suggest ranges are 0.01–30%, preferably 0.05–25%, more preferably 0.1–20% by weight of the total composition. The oil may be volatile or nonvolatile. The term "volatile" means that the oil has a measureable vapor pressure, or a vapor pressure of greater than 2 mm. of mercury at 20° C. The term "nonvolatile" means that the oil does not have a measureable vapor pressure, i.e. a vapor pressure of less than about 2 mm. mercury at 20° C.

(a) Volatile Oils

Examples of volatile oils include volatile solvents which generally have a viscosity of 0.5 to 10 centipoise at 25° C. Suitable volatile oils include linear silicones, cyclic silicones, paraffinic hydrocarbons, or mixtures thereof. Cyclic silicones (or cyclomethicones) are of the general formula:

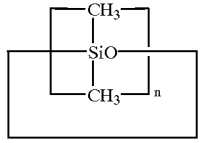

where n=3–7.

Linear volatile silicones in accordance with the invention have the general formula:

$(CH_3)_3Si-O-[Si(CH_3)_2-O]_n-Si(CH_3)_3$ where n=0–6, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Also suitable as the volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and C8 20 isoparaffins as disclosed in U.S. Patent Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic ydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable.

(b) Nonvolatile Oils

Also suitable are nonvolatile oils which are liquids at room temperature and preferably have a viscosity in the range of about 10 to 500,000, preferably 75–300,000, most preferably 100–200,000 centipoise at 25° C. A variety of nonvolatile oils may be found in the non-aqueous phase of the composition.

Examples of suitable nonvolatile oils include guerbet esters, which are generally defined as esters which are formed by the reaction of a guerbet alcohol (which is a branched chain alcohol) having the general formula:

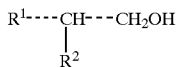

with a carboxylic acid having the general formula:

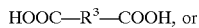

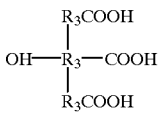

wherein $R^1$ and $R^2$ are each independently a $C_{4-20}$ alkyl and each $R^3$ is a substituted or unsubstituted $C_{,50}$ straight or branched chain alkyl or alkylene group, or phenyl, wherein the substituents are halogen, hydroxyl, carboxyl, or alkylcarbonyloxy. Preferred are guerbet esters which are the reaction product of a guerbet alcohol as identified above, and a compound of the formula:

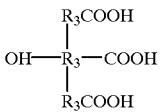

wherein each $R_3$ is independently a $C_{1-10}$ straight or branched alkyl or alkylene. Preferably each $R_3$ is $C_1$ alkyl or alkylene, e.g. the compound is citric acid (2-hydroxy-1,2,3-propanetricarboxylic acid). Examples of such guerbet esters are those disclosed in U.S. Pat. No. 4,868,236, which is hereby incorporated by reference. One example of such a nonvolatile oil is trioctyldodecyl citrate, which is sold by Phoenix Chemical Inc. under the tradename Pelemol TGC. Trioctyl dodecyl citrate has the following general formula:

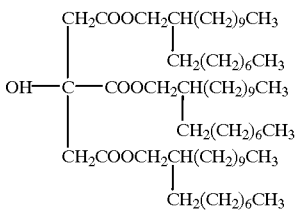

Also preferred is another guerbet ester referred to as trioctyldodecyl citrate dilinoleate which is sold by Phoenix Chemical Inc., under the tradename Pelemol C-150.

Other examples of nonvolatile oils suitable for use in the compositions of the invention include esters of the formula RCO—OR' wherein R and R' are each independently a $C_{1-25}$, preferably a $C_{4-20}$, straight or branched chain alkyl, alkenyl or alkoxycarbonylalkyl or alkylcarbonyloxyalkyl. Preferred are esters which are the reaction product of of a branched chain fatty acid and a branched or straight chain fatty alcohol, preferably a branched chain fatty alcohol. Examples of such esters include isotridecyl isononanoate, isostearyl neopentanoate, tridecyl neopentanoate, cetyl octanoate, cetyl ricinoleate, decyl isostearate, isodecyl oleate, isodecyl neopentanoate, isohexyl neopentanoate, tridecyl octanoate, and so on.

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Nonvolatile silicones, both water soluble and water insoluble, are also suitable as the oil component. Suitable water insoluble nonvolatile silicones include amodimethicone, dimethicone, phenyl trimethicone, and mixtures thereof provided such silicones are nonpolar materials which are soluble or dispersible in the nonaqueous phase.

Also suitable as the nonvolatile oil are various fluorinated oils such as fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin.

The non-aqueous phase may contain other ingredients which as soluble or dispersible in the non-aqueous phase.

II. The Aqueous Phase

The aqueous phase of the composition may comprise from 0.1–99.5%, preferably 0.5–90%, more preferably 1–75% by weight of the total composition. The aqueous phase may be the continuous phase in the emulsion, or it may be the dispersed phase so that the compositions may be in the form of a water-in-oil or oil-in-water emulsion. Preferably the compositions of the invention are in the form of an oil-in-water emulsion where the aqueous phase the continuous phase and the non-aqueous phase forms the dispersed phase of the composition.

III. Pigments and Particulate Fillers

The composition of the invention is a pigmented emulsion composition, and comprises from about 0.01–40%, preferably 0.05–35%, more preferably 0.1–30% by weight of the total composition of one or more pigments either alone or in combination with particulate fillers (together referred to as "particulate matter"). Preferably, the particulate matter has a particle size of 0.02 to 100, preferably 0.5 to 100, microns. The particulate matter may be colored or non-colored (for example white). Suitable particulates include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silk powder, silica, talc, mica, titanium dioxide, zinc laurate, zinc myristate, zinc rosinate, alumina, attapulgite, calcium carbonate, calcium silicate, dextran, kaolin, nylon, silica silylate, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

The particulates may also include various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof.

Preferably the composition will contain both pigmented and non-pigmented particulates. Obviously the percentage of pigments used in the particulate phase will depend on the type of cosmetic being formulated. Color cosmetics generally have a much higher concentration of color than other types of cosmetics. Generally the weight ratio of pigmented to non-pigmented particulates range from 1:50 to 50:1. It should be noted that particulates that are white or have no color are considered non-pigmented particulates in accordance with the invention, while particulates which exhibit color other than white are considered pigmented particulates in accordance with the invention.

IV. Other Ingredients

The compositions of the invention may comprise a variety of other ingredients which may be found in the aqueous or non-aqueous phases of the composition, depending on whether the ingredients are soluble in that phase.

A. EMULSIFIERS OR SURFACTANTS

Preferably, the composition of the invention comprises one or more emulsifiers or surfactants which aid in forming and maintaining a stable emulsion composition. Suggested amounts of emulsifiers range from about 0.01–15%, preferably 0.05–10%, more preferably 0.1–8% by weight of the total composition. Suitable emulsifiers may be anionic, non-ionic, amphoteric, or cationic in nature.

1. Anionic Emulsifiers

Particularly suitable anionic emulsifiers for use in the compositions may be referred to as carboxylated salts. The term "carboxylated salt" means the reaction product of a salt with a compound containing at least one carboxylic acid group. Preferably the carboxylated salt is the salt of a water insoluble fatty acid and a base. While the fatty acid used to make the carboxylated salt gelling agent is generally water insoluble, the resulting gelling agent may be water soluble or water insoluble. Preferably, the carboxylated salt used in the compositions of the invention are water soluble. Suitable fatty acids used to make the carboxylated salt are $C_{12-40}$ straight or branched chain, saturated or unsaturated fatty acids. Suitable fatty acids include lauric, myristic, palmitic, stearic, oleic, linoleic, linolenic, behenic, caprylic, stearic, and so on. In addition, oils containing fatty acid mixtures, such as palm kernel, olive, tallow, peanut, rapeseed, and the like may be used as the fatty acid component. Preferred are $C_{16-22}$ fatty acids such as lauric, stearic, or behenic. Most preferred is where the fatty acid is stearic acid.

A variety of cations may be used. Generally the type of cation selected will determine whether the resulting gelling agent is water soluble or water insoluble. Generally cations such as sodium, potassium, or low molecular weight amines or alkanolamines will provide water soluble gelling agents. Suitable amines are ammonia and derivatives thereof. Suitable alkanolamines include mono- di- and triethanolamines. Preferably, the salt is an alkanolamine, in particular triethanolamine.

Examples of gelling agents which may be used in the compositions of the invention are sodium, potassium, aluminum, magnesium, calcium, or amine salts of stearic, behenic, caprylic, tallowic, tallic, cocoic, or lauric acids, and so on. Preferably the gelling agent used in the compositions of the invention are water soluble salts of fatty acids and alkanolamines, and in particular TEA stearate.

2. Nonionic Surfactants or Emulsifiers

Preferably the composition comprises one or more nonionic surfactants which aid in maintaining a stable emulsion. Preferably, the nonionic surfactants range from about 0.01–10%, preferably 0.05–5%, more preferably 0.1–3% by weight of the total composition. A variety of nonionic surfactants are suitable.

Suitable nonionic surfactants include alkoxylated alcohols, or ethers, formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, Oleth 1-100 which is formed by the reaction of oleyl alcohol and ethylene oxide, and so on. If desired, the alkoxylated alcohol may be reacted with one or more salts such as sodium, potassium phosphate, and the like.

Particularly preferred for use in the composition of the invention is Oleth-3, which is the reaction product of oleyl alcohol and ethylene oxide; either alone or in combination with a salt of Oleth-3.

Also suitable as the nonionic surfactant are alkyoxylated carboxylic acids, which are formed by the reaction of a carboxylic acid with an alkylene oxide or with a polymeric ether. The resulting products have the general formula:

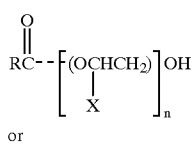

or

-continued

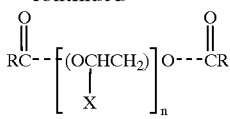

where RCO is the carboxylic ester radical, X is hydrogen or lower alkyl, and n is the number of polymerized alkoxy groups. In the case of the diesters, the two RCO- groups do not need to be identical. Preferably, R is a $C_{6-30}$ straight or branched chain, saturated or unsaturated alkyl, and n is from 1–100.

Also suitable as the nonionic surfactant are monomeric, homopolymeric and block copolymeric ethers. Such ethers are formed by the polymerization of monomeric alkylene oxides, generally ethylene or propylene oxide. Such polymeric ethers have the following general formula:

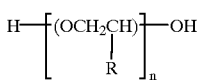

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

Also suitable as nonionic surfactants are silicone surfactants, which are defined as silicone polymers which have at least one hydrophilic radical and at least one lipophilic radical. Examples of such silicone surfactants are disclosed in U.S. Pat. No. 5,725,845, which is hereby incorporated by reference.

B. Water Soluble or Water Dispersible Thickeners

If desired, the compositions may comprise one or more water soluble or water dispersible thickening agents in a range of about 0.01–10%, preferably 0.05–8%, more preferably 0.1–5% by weight of the total composition. Suitable thickeners are preferably organic ingredients and include cellulose derivatives and gums such as galactans, galactomannans, glucomannans, polyuronic acids, heteropolysaccharides, and the like. Suitable galactans are agar, agarose, kappa carageenan, iota carageenan, lambda carageenan, and the like. Examples of suitable galactomannans are locust bean gum and guar; examples of glucans are cellulose and derivatives thereof, starch and derivatives, dextrans, pullulan, beta 1,3-glucans, chitin, xanthan, tamarind and the like; examples of glucomannans are konjac; examples of polyuronlc acids are algin, alginates, pectins; examples of heteropolysaccharides are gellan, welan, acacia gum, gum arabic, karaya gum, okra gum, aloe gum, gum tragacanth, gum ghatti quinceseed gum, psyllium, starch arabinogalactan and so on. Also suitable are dextran sulfate, heparin, pectin, sodium alginate, and mixtures thereof. Preferred are heteropolysaccharides, in particular acacia gum.

C. Film Formers

Preferably, the composition comprises one or more film formers which, upon drying, will form a continuous film on the lashes or brows. The film former may be present ranging from 0.1–45%, preferably 0.5–20%, more preferably 1–15% by weight of the total composition. The film formers may be resinous plant extracts or synthetic polymers.

1. Resinous Plant Extracts

Examples of resinous plant extracts that provide film forming properties include materials such as rosin and shellac, or derivative thereof.

2. Synthetic Polymers

The synthetic polymer will cause the composition to give an improved film on the lashes or brows, and may also cause improved transfer resistance and/or plasticity of the film and improved adhesion of the film to the surface. In addition, the synthetic polymers either alone or in combination with the vegetable wax will cause the lashes to curl. Suitable amounts of synthetic polymer may range from about 0.1–40%, preferably 0.5–35%, more preferably 1–30% by weight of the total composition.

The synthetic polymer may be a liquid or solid at 25° C., and is often found in the form of an aqueous dispersion where the polymer particles are dispersed in the aqueous phase of the polymer emulsion. A variety of synthetic polymers are suitable, including homo- or copolymers of monomers such as acrylic acid, methacrylic acid or $C_{1-30}$ esters of acrylic or methacrylic acid, vinyl pyrrolidone, vinyl acetate, urethane, $C_{1-30}$ hydroxy esters of acrylic or methacrylic acid, vinyl isodecanoate, styrene, and olefins such as ethylene, propylene, butene, pentene, decene, hexadecene, and so on. The synthetic polymers may be homo- or copolymers of the monomer units mentioned above. In addition, one or more of the above mentioned monomers may be copolymerized with various organic compounds such as polyalkylene glycols, paraffinic hydrocarbons, alkoxylated alcohols and the like.

Preferred are homopolymers of urethane and copolymers of vinyl acetate and acrylic acid, methacrylic acid, and their simple esters. Preferred homopolymers of urethane are available from BASF under the tradename Luviset® P.U.R., which has the CTFA name Polyurethane 1. This material is available as an aqueous emulsion in water having a solids content of 28 to 32% by weight of the polymer emulsion. The other preferred synthetic film forming polymer is acrylate copolymer emulsion in water sold by Air Products and Chemicals, Inc. under the tradename Flexbond® 381 Emulsion Polymer, which is described as a formaldehyde free vinyl acrylic copolymer.

D. Vitamins

The compositions of the invention may contain vitamins and/or coenzymes, as well as antioxidants. If so, 0.001–10%, preferably 0.01–8%, more preferably 0.05–5% by weight of the total composition are suggested. Suitable vitamins include the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D, C, and K, as well as derivatives thereof are suitable. Particularly preferred are derivatives of vitamins C, E, and A such as magnesium ascorbyl phosphate, retinyl palmitate, tocopheryl acetate, and mixtures thereof.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

E. Biological Additives

The composition may comprise one or more biological additives. Suggest ranges are about 0.001–8%, preferably 0.01–6%, more preferably 0.05–5% by weight of the total composition. Suitable biological additives include extracts of plant or animal matter. Examples of desireable biological additives include hydrolysates of plant or animal extracts such as hydrolyzed keratin, hydrolyzed wheat protein and derivatives thereof, such as copolymers of the hydrolysates with monomers such as vinyl pyrrolidone, vinyl acetate, and the like. Particularly preferred are keratin and wheat polypeptides, in particular, keratin polypeptides having a molecular weight of less than about 1000 daltons. Such keratin polypeptides are sold by Croda under the tradename Crotein SKP, which is a hydrolyzed keratin having an approximate molecular weight of about 600.

F. Preservatives

Preferably the composition comprises one or more preservatives in ranges of about 0.001–10%, preferably 0.005–8%, more preferably 0.01–5% by weight of the total composition. Examples of suitable preservatives are parabens, such as methyl, ethyl, and propyl parabens, and the like.

The compositions of the invention are used to lengthen, color, thicken, and curl eyelashes. The compositions cause from 50 to 73% increase in the radius of curvature of the eyelash when compared to the untreated eyelash.

The invention will be further described in connection with the following examples which are set forth for the purposes of illustration only.

EXAMPLE 1

A mascara composition were made according to the following formula:

|   |   | w/w % 1 |
|---|---|---|
| 1 | Water | 40.05 |
| 2 | Acacia gum | 3.00 |
| 3 | Trisodium EDTA | 0.05 |
| 3 | Black iron oxide | 11.0 |
| 3 | Triethanolamine | 2.00 |
| 4 | Oleth-3-phosphate | 0.50 |
| 5 | Rice Wax | 2.00 |
| 5 | Oleth-3 | 1.80 |
| 5 | Ditrimethylolpropane tetrastearate | 5.00 |
| 5 | Polyethylene | 8.00 |
| 5 | Trioctyldodecyl citrate dilinoleate | 0.50 |
| 6 | Stearic acid | 4.30 |
| 6 | N-acyl glutamic acid diamide | 1.40 |
| 7 | Propyl paraben | 0.10 |
| 8 | Phenoxyethanol | 1.00 |
| 8 | Butylene glycol | 2.00 |
| 8 | Methyl paraben | 0.30 |
| 9 | Acrylate copolymer emulsion* | 12.00 |
| 10 | Polyurethane** | 5.00 |

Sequences 1 and 2 were pre-mixed at room temperature until the acacia gum was dispersed in the water. Sequences 1 through 4 were ground in a colloid mill until the pigments were dispersed in the mixture (approximately 10 minutes). Sequences 5 and 6 were heated on a hot plate with continuous stirring at a temperature of approximately 110° C. until the mixture became clear, light yellow. The mixture was allowed to cool to 85 to 90° C., and Sequence 7 was then added with mixing. When the mixture was cooled to 40 to 45° C. Sequence 8 was added. The mixture was heated to 50° C. and Sequence 9 added. When the temperature of the mixture reached 60° C. Sequence 10 was added. The mixture was cooled to room temperature and filled into mascara containers.

EXAMPLE 2

A total of 13 panelists tested the mascara of Example 1. Prior to application of the mascara, the curvature of both the panelist's eyelashes was measured by taking close-up side view digital photographs using a Nikon E2N digital camera, having a 105 mm. macro lens and twinflash. The camera was set to A: Aperature-Priority Auto Mode. At an aperature of F38, the shutter speed was automatically set. The macro lens was set at a reproduction ratio of 1:5. A close up image of each lash was taken at a 90 degree oblique angle to the face (a side shot) prior to application of mascara in order to obtain a baseline measurement for lash curling. The panelist then applied mascara to both lashes and photographs of the left and right eyelashes were taken immediately after, then eight hours after, application of mascara. The digitized photographs were stored on a disk.

Using Image Pro Plus 4.0 software, the close up photographs were analyzed by measuring the curvature of the lashes for each panelist before, immediately after, and eight hours after application of mascara. For each panelist, the curvature of right and left lashes before (baseline), immediately after, and eight hours after mascara application, was measured by selecting a circle having a radius which best approximated the curvature of the lash being evaluated. Lash curvature was calculated by taking the reciprocal of the radius for each measurement. For example, if a panelist's lash curvature, prior to mascara application, most closely approximated a circle having a radius of 5.5 mm., then the baseline curvature would be 1/5.5. Similarly, a panelist's lash curvature, immediately after application of mascara, most closely approximated a circle having a radius of 4.5 mm., then the immediate curvature would be 1/4.5. Further, if a panelist's lash curvature, eight hours after application of mascara, most closely approximated a circle having a radius of 4.2 mm., then the eight hour curvature would be 1/4.2.

The percentage change from basline was calculated as follows:

$$\% \text{ immediate curvature} = \frac{(\text{immediate curvature} - \text{baseline curvature}) \times 100}{\text{baseline curvature}}$$

$$\% \text{ eight hour curvature} = \frac{(\text{eight hour curvature} - \text{baseline curvature}) \times 100}{\text{baseline curvature}}$$

The following results were obtained:

|   | % Immediate | % Eight Hour |
|---|---|---|
| Panelist 1 |   |   |
| Right Lash | 41.81 | 76.76 |
| Left Lash | 36.71 | 58.82 |
| Panelist 2 |   |   |
| Right Lash | 32.43 | 37.38 |
| Left Lash | 100.60 | 110.62 |

-continued

|  | % Immediate | % Eight Hour |
|---|---|---|
| Panelist 3 | | |
| Right Lash | 139.39 | 188.02 |
| Left Lash | 141.82 | 20.91 |
| Panelist 4 | | |
| Right Lash | 110.44 | 173.57 |
| Left Lash | 165.93 | 163.04 |
| Panelist 6 | | |
| Right Lash | 162.90 | 185.96 |
| Left Lash | 50, 34 | 77.78 |
| Panelist 7 | | |
| Right Lash | 140.48 | 20.96 |
| Left Lash | −34.87 | −63.33 |
| Panelist 8 | | |
| Right Lash | 96.50 | 134.17 |
| Left Lash | 82.26 | 56.94 |
| Panelist 9 | | |
| Right Lash | 107.03 | 204.60 |
| Left Lash | 122.70 | 143.41 |
| Panelist 10 | | |
| Right Lash | 11.65 | 90.74 |
| Left Lash | −18.24 | −35.35 |
| Panelist 11 | | |
| Right Lash | 12.11 | −32.38 |
| Left Lash | −9.96 | −4.82 |
| Panelist 12 | | |
| Right Lash | 106.72 | 61.05 |
| Left Lash | 29.67 | 15.69 |
| Panelist 13 | | |
| Right Lash | 108.85 | 100.50 |
| Left Lash | 28.33 | 12.00 |
| Panelist 14 | | |
| Right Lash | 37.14 | 73.49 |
| Left Lash | 43.63 | 37.78 |
| Mean | 71.01 | 73.40 |
| Std. Dev. | 11.15 | 14.18 |

The above results illustrate that the compositions of the invention cause improvement in lash curling that is significant at the 95% confidence level. In particular, the compositions of the invention will provide from about 25 to 100%, preferably, of improvement in lash curl.

Improvement was observed up to 8 hours after application.

EXAMPLE 3

A mascara composition was made according to the following formula:

|  |  | w/w % |
|---|---|---|
| 1 | Water | QS |
| 2 | Acacia gum | 1.9608 |
| 4 | Butylene glycol | 2.9412 |
| 3 | Methyl paraben | 1.9608 |
| 3 | Triethanolamine | 1.9608 |
| 3 | Black iron oxide | 10.7843 |
| 3 | Trisodium EDTA | 0.0490 |
| 3 | Silk Powder | 0.0490 |

-continued

|  |  | w/w % |
|---|---|---|
| 3 | Hydrolyzed keratin | 0.0490 |
| 4 | Oleth-3-phosphate | 0.4902 |
| 5 | Rice wax | 1.9608 |
| 5 | Ditrimethylolpropane tetrastearate | 4.9020 |
| 5 | Polyethylene | 7.8431 |
| 5 | Ditrioctyldodecyl citrate | 0.4902 |
| 5 | Oleth-3 | 1.7647 |
| 6 | Stearic acid | 4.2157 |
| 6 | Dibutyl lauroyl glutamide | 1.3725 |
| 7 | Propyl paraben | 0.0980 |
| 8 | Phenoxyethanol | 0.9804 |
| 9 | Acrylic copolymer emulsion* | 11.7647 |
| 10 | Polyurethane-1** | 4.9020 |
| 11 | Retinyl palmitate | 0.0490 |
| 11 | Tocopheryl acetate | 0.0490 |
| 12 | PVP/hydrolyzed wheat protein | 0.0980 |

*Flexbond ® 381 Emulsion Polymer - formaldehyde free vinyl acrylic copolymer, Air Products and Chemicals, Inc.
**Luviset ® P.U.R., Polyurethane 1, BASF.

Sequences 1 and 2 were pre-mixed at room temperature until the acacia gum was dispersed in water. Sequences 1 through 4 were ground in a colloid mill until the pigments were dispersed in the mixture (approximately 10 minutes). Sequences 5 and 6 were heated on a hot plate with continuous stirring at a temperature of approximately 110° C. until the mixture became clear, light yellow. The mixture was allowed to cool to 85 to 90° C., and Sequence 7 was then added with mixing. When the mixture was cooled to 40 to 45° C. Sequence 8 was added. The mixture was heated to 50° C. and Sequence 9 added. When the temperature of the mixture reach 60° C. Sequences 10, 11, and 12 were added. The mixture was cooled to room temperature and filled into mascara containers.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A pigmented emulsion composition for application to eyelashes or eyebrows comprising 0.1–99.5% aqueous phase and 0.1–99% non-aqueous phase, wherein the non-aqueous phase comprises at least one organic, solid, non-polymeric gelling agent selected from the group consisting of:
   a. N-acyl amino acids, or esters, or amides thereof;
   b. 12-hydroxystearic acid and esters and amides thereof,
   c. fatty acid esters of di- or triffunctional alcohol dimers;
   d. alkylamides of di- and tricarboxylic acids; and
   e. mixtures thereof
which is capable of gelling the pigmented emulsion composition to a viscosity of 4,000 to 2,000,000 centipoise at 25° C.

2. The composition of claim 1 wherein the gelling agent comprises an N-acyl amino acid or ester or amide thereof.

3. The composition of claim 2 wherein the gelling agent comprises an N-acyl amino acid amide.

4. The composition of claim 3 wherein the gelling agent comprises N-acyl glutamic acid diamide.

5. The composition of claim 1 wherein the gelling agent comprises a fatty acid ester of a trifunctional alcohol dimer.

6. The composition of claim 5 wherein the trifunctional alcohol dimer is a dimer of trimethylolpropane.

7. The composition of claim 6 wherein dimer of trimethylolpropane is ditrimethylolpropane tetrastearate.

8. The composition of claim 1 wherein the nonaqueous phase further comprises 0.1–50% by weight of the total composition of one or more waxes.

9. The composition of claim 1 wherein the wax comprises synthetic wax, and the composition contains less than about 2% by weight of animal, vegetable, or mineral wax.

10. The composition of claim 9 wherein the synthetic wax is polyethylene.

11. The composition of claim 1 wherein the nonaqueous phase further comprises 0.1–30% by weight of the total composition of one or more oils.

12. The composition of claim 11 wherein the oil comprises a nonvolatile oil.

13. The composition of claim 12 wherein the oil comprises a guerbet ester.

14. The composition of claim 1 further comprising 0.01–40% by weight of the total composition of particulates.

15. The composition of claim 1 further comprising 0.01–15% by weight of the total composition of one or more emulsifiers.

16. The composition of claim 1 further comprising 0.1–10% of one or more water soluble thickeners.

17. The composition of claim 1 further comprising 0.1–40% by weight of the total composition of one or more synthetic film forming polymers.

18. A method for lengthening, coloring and curling eyelashes comprising applying to said eyelashes a pigmented emulsion composition for application to eyelashes or eyebrows comprising 0.1–99.5% aqueous phase and 0.1–99% non-aqueous phase, wherein the non-aqueous phase comprises at least one organic, solid, non-polymeric gelling agent selected from the group consisting of:

a. N-acyl amino acids, or esters, or amides thereof;

b. 12-hydroxystearic acid and esters and amides thereof, c. fatty acid esters of di- or trifunctional alcohol dimers;

d. alkylamides of di- and tricarboxylic acids; and e. mixtures thereof which is capable of gelling the pigmented emulsion composition to a viscosity of 4,000 to 2,000,000 centipoise at 25° C.

* * * * *